United States Patent [19]

Schroeppel

[11] Patent Number: 4,802,481

[45] Date of Patent: Feb. 7, 1989

[54] APPARATUS FOR CONTROLLING PACING OF A HEART IN RESPONSE TO CHANGES IN STROKE VOLUME

[75] Inventor: Edward A. Schroeppel, Miramar, Fla.

[73] Assignee: Cordis Leads, Inc., Miami, Fla.

[21] Appl. No.: 97,817

[22] Filed: Sep. 17, 1987

Related U.S. Application Data

[62] Division of Ser. No. 885,063, Jul. 14, 1986, Pat. No. 4,708,143, which is a division of Ser. No. 632,625, Jul. 19, 1984, Pat. No. 4,600,017.

[51] Int. Cl.$^4$ ............................................. A61N 1/36
[52] U.S. Cl. .............................................. 128/419 PG
[58] Field of Search ........ 128/419 D, 419 P, 419 PG, 128/675, 784, 785, 786

[56] References Cited

U.S. PATENT DOCUMENTS

| | | | |
|---|---|---|---|
| 3,614,954 | 10/1971 | Mirowski | 128/419 D |
| 3,815,611 | 6/1974 | Denniston, III | 128/419 D |
| 4,052,991 | 10/1971 | Zacouto | 128/419 PG |
| 4,191,193 | 3/1980 | Seo | 128/675 |
| 4,303,075 | 12/1981 | Heilman et al. | 128/419 PG |
| 4,428,378 | 1/1984 | Anderson et al. | 128/419 PC |
| 4,458,695 | 7/1984 | Peers-Trevarton | 128/786 |
| 4,469,104 | 9/1984 | Peers-Trevarton | 128/419 P |
| 4,485,813 | 12/1984 | Anderson et al. | 128/675 |
| 4,527,568 | 7/1985 | Rickards | 128/419 PG |
| 4,535,774 | 8/1985 | Olson | 128/419 PG |
| 4,566,456 | 1/1986 | Koning et al. | 128/675 |
| 4,686,987 | 8/1987 | Salo et al. | 128/419 PG |

Primary Examiner—William E. Kamm
Attorney, Agent, or Firm—Thomas R. Vigil

[57] ABSTRACT

The apparatus is used for sensing opening and closing of a tricuspid valve in a heart, for using those sensings to determine stroke volume, and for controlling pacing of a heart relative to changes in stroke volume. The apparatus comprises a pacer, a pacing lead coupled to the pacer and having a lead body, a pressure sensor mounted in the lead body and a pacing electrode, circuit means in the pacer coupled to the sensor for sensing the opening of the tricuspid valve during each heart cycle and for sensing the closing of the tricuspid valve during each heart cycle; means for calculating ejection time from the openings and closings of the tricuspid valve; means for calculating the change in ejection time, $\Delta ET$, from calculations of ejection time; means for calculating changes in stroke volume, $\Delta SV$, means for determining the required change in heart rate, $\Delta R$, relative to the change in stroke volume, $\Delta SV$; and means for adjusting the pacing rate of said pacer relative to the required change in heart rate, $\Delta R$.

3 Claims, 3 Drawing Sheets

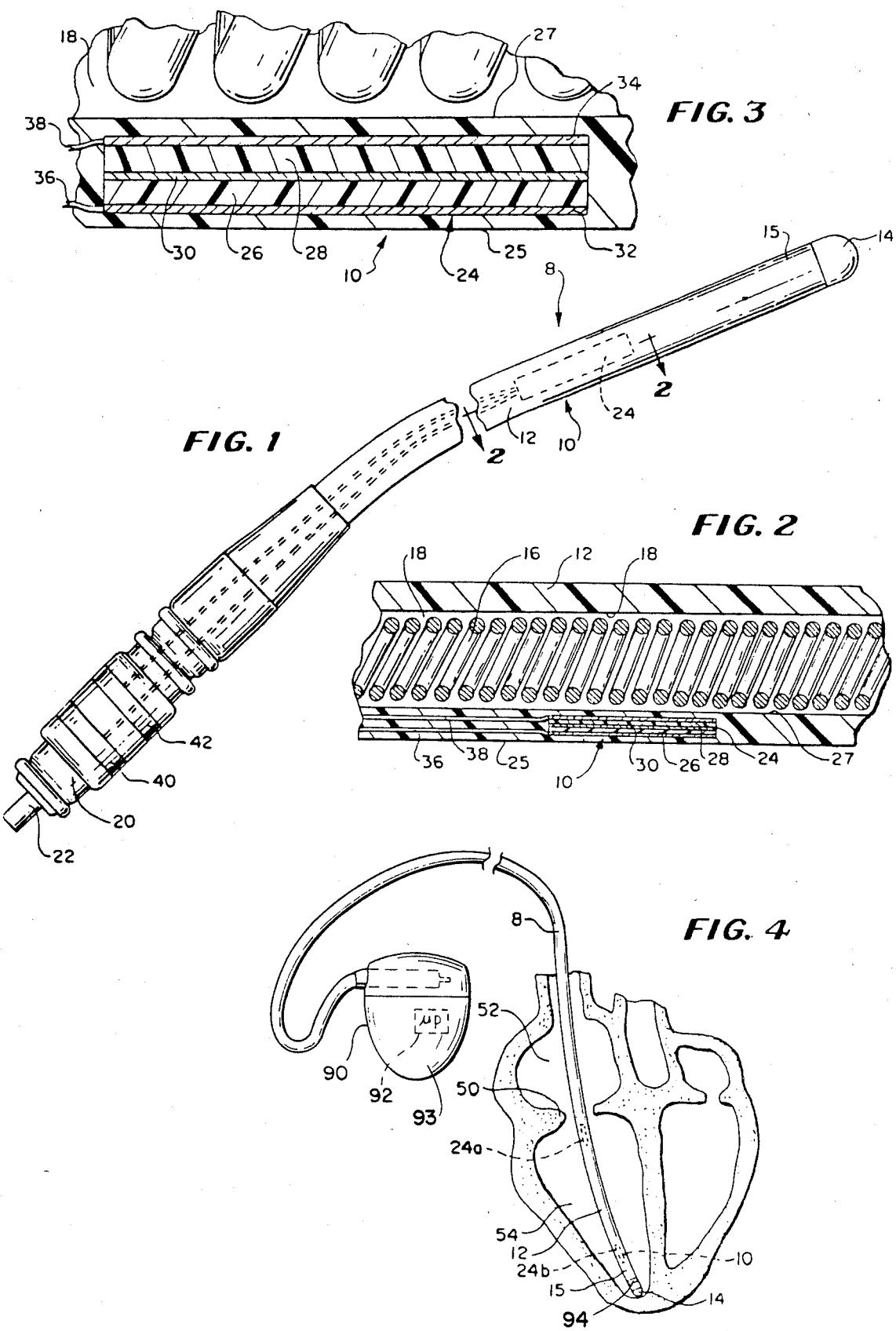

APPARATUS FOR CONTROLLING PACING OF A HEART IN RESPONSE TO CHANGES IN STROKE VOLUME

CROSS-REFERENCE TO RELATED APPLICATIONS

This application is a division of application Ser. No. 885,063 filed July 14, 1986, for: METHOD FOR CONTROLLING PACING OF A HEART IN RESPONSE TO CHANGES IN STROKE VOLUME, issued to U.S. Pat. No. 4,708,143 on Nov. 24, 1987; which is a division of application Ser. No. 632,625 filed July 19, 1984, issued to U.S. Pat. No. 4,600,017 on July 15, 1986 for: PACING LEAD WITH SENSOR.

BACKGROUND OF THE INVENTION

1. Field of the Invention

This invention relates to a pacing lead with sensor mounted therein for measuring the occurrence of a phenomenon in a living organism, and more particularly, to a pacing lead having a piezoelectric sensor, the pacing lead being implanted in a living organism whereby the phenomenon acting on the sensor will generate an electric waveform indicative of the phenomenon. The phenomenon sensed is typically contractions of the heart.

2. Description of the Prior Art

Heretofore, various sensors have been developed for sensing phenomena occurring in living organisms, and particularly, the human body and heart. For example, cardiac sensors are disclosed in U.S. Pat. Nos. 2,634,721; 3,038,465; 3,410,441; 3,811,427 and 3,831,588. These sensors have utilized various complicated constructions, such as strain gauges in U.S. Pat. Nos. 2,976,865 and 4,003,370, field effect transistors in U.S. Pat. No. 3,946,724, PN type transducers in U.S. Pat. No. 3,710,781, and signal generating semiconductor devices in U.S. Pat. No. 3,811,427.

Further, it has been experimentally suggested to use piezoelectric sensors for measuring heart beats and blood flow by wrapping a band of piezoelectric material around a patient's chest or leg, including those of the ferroelectric polymer and polyvinylidene fluoride (PVF$_2$) types. For example, see "Ferroelectric Polymers and their Application" by Micheal A. Marcus, appearing in Ferroelectronics: 40, 1982, and "Piezoelectric High Polymer Foils as Physiological Mechanic-Electric Energy Converters" by E. Hausler, H. Lang and F. J. Schreiner, appearing in IEEE 1980 Bio Medical Group Annual Conference, Frontiers of Engineering in Health Care.

Further, it is known to implant a piezoelectric device in a living organism for other purposes, such as to: power a cardiac or other pacer as suggested in U.S. Pat. No. 3,659,615, and control or vary the pacing rate with the implantee's own physical activity as disclosed in U.S. Pat. No. 4,140,132.

It has also been known that under controlled clinical conditions one can, by replacing a microphone on the chest of a person, measure the vibrations of the heart and obtain graphs of waveforms showing, at a minimum, the opening and closing of the heart valves. See, for example, "The Analysis and Interpretation of the Vibrations of the Heart, as a Diagnostic Tool and Physiological Monitor" by C. M. Agress, M.D. and L. G. Fields appearing in IRE Transactions on Biomedical Electronics, July 1961.

As will be described in greater detail hereinafter, it has been found from studies on dogs using a pacing lead having a piezoelectric sensor mounted in the distal end portion thereof in accordance with the teachings of the present invention, that graphs of waveforms can be obtained clearly showing the opening and closing of the heart valves. This can be significant since from measurements of opening and closing of the heart valves, one can determine stroke volume and then by multiplying stroke volume by heart rate, one can determine cardiac output.

Also as will be described in greater detail hereinafter, the present invention provides an apparatus for controlling pacing of a heart relative to the changes in stroke volume using the pacing lead having a lead body and a pressure sensor mounted in the lead body near the end of the pacing lead. With this apparatus, openings and closing of a tricuspid valve in a heart are sensed by the sensor and such sensings are used to determine stroke volume.

Heretofore it has been proposed in Mirowski et al, U.S. Pat. No. 3,614,954 to mount a pressure sensing bulb on the outside of a pacing lead for the purpose of sensing pressure. These sensings are used to determine malfunctions of the heart so that the heart can be automatically defibrillated by sending electrical pulses to electrodes on the pacing lead from an electronic standby defibrillator electrically coupled to the pressure sensing bulb.

In the Denniston, III U.S. Pat. No. 3,815,611 an apparatus using a piezoelectric sensor is disclosed for sensing or detecting contractions of the muscles of living animals.

In the Zacouto U.S. Pat. No. 4,052,991 there is disclosed a method of stimulating a heart in response to pressure sensings sensed by a pressure detector mounted in the intraventricular septum of the heart, as shown in FIG. 19 of this patent.

In the Seo U.S. Pat. No. 4,191,193 there is disclosed a catheter head-type transducer for measuring pressure in a vessel of a body.

In the Anderson et al. U.S. Pat. No. 4,428,378, the disclosure of which is incorporated herein by reference, a rate adaptive pacer is disclosed which includes an activity sensor mounted within the pacer for detecting the general activity level of a patient and for then altering the escape interval of the pacer between a preset minimum and maximum in response to the detected activity level of the patient. The pacer includes signal processing circuitry which utilizes the sensed activity for controlling the rate of pacing.

In the Anderson et al. U.S. Pat. No. 4,485,813 there is disclosed in implantable dynamic pressure transducer system for detecting pressure and other force parameters for use with a pacemaker or other implanted cardiac monitoring and/or treatment device.

Finally, in the Olson U.S. Pat. No. 4,535,774 there is disclosed a stroke volume controlled pacer which employs a pacing lead having electrodes thereon positioned within a heart chamber for sensing changes in impedance in the heart chamber. Then, the changes in impedance in the heart chamber are used to infer stroke volume. This patent also suggests that stroke volume may be inferred by a variety of measurements taken in the right or left heart and including pressure-time histories of arterial blood flow, as well as direct flow measurements in the major blood vessels of the heart.

As will be described in greater detail hereinafter, the apparatus of the present invention does not utilize pressure-time histories of arterial blood flow, direct flow measurements in major blood vessels of the heart or changes in impedance within a heart chamber. Instead, the apparatus of the present invention utilizes sensings of the opening and closing of the tricuspid valve for determining ejection time and then from determinations of ejection time determining stroke volume and changes in stroke volume. The changes in stroke volume are utilized for controlling the pacing of a heart.

SUMMARY OF THE INVENTION

According to the invention there is provided an apparatus for sensing pressure changes in a heart chamber to determine opening and closing of a tricuspid valve in a heart, for using those determinations of openings and closings of the tricuspid valve to determine stroke volume and changes in stroke volume, and for controlling pacing of a heart relative to changes in stroke volume, said apparatus comprising: a pacer having therein pulse generating circuitry for generating pacing pulses, control circuitry for controlling the pulse generating circuitry and a socket; a pacing lead having a proximal termination received in said pacer socket, being electrically coupled to said pacer in said socket and having a lead body; a pressure sensor mounted in said lead body; a pacing electrode on said lead body; means for establishing a pacing circuit including said pacing electrode, said pulse generating circuitry and said control circuitry; said control circuitry including circuit means in said pacer coupled to said sensor for sensing changes in pressure in a heart chamber to determine the opening of a tricuspid valve during each heart cycle and the closing of the tricuspid valve during each heart cycle; means for calculating ejection time from the openings and closing of the tricuspid valve; means for calculating the change in ejection time, $\Delta ET$, from calculations of ejection time; means for calculating changes in stroke volume, $\Delta SV$ from calculations of ejection time; means for determining the required change in heart rate, $\Delta R$, relative to the change in stroke volume, $\Delta SV$; and means in said control circuitry for adjusting the pacing rate of said pacer relative to the required change in heart rate, $\Delta R$.

BRIEF DESCRIPTION OF THE DRAWINGS

FIG. 1 is a plan view of a pacing lead with sensor constructed according to the teachings of the present invention.

FIG. 2 is an enlarged cross-sectional fragmentary view of the lead with sensor shown in FIG. 1 and is taken along line 2—2 of FIG. 1.

FIG. 3 is a further enlarged fragmentary view of a portion of FIG. 2.

FIG. 4 is a cross-sectional view of a human heart showing the pacing lead with sensor inserted into the heart in a pacer connected to the lead.

DESCRIPTION OF THE PREFERRED EMBODIMENT

Figure 5:
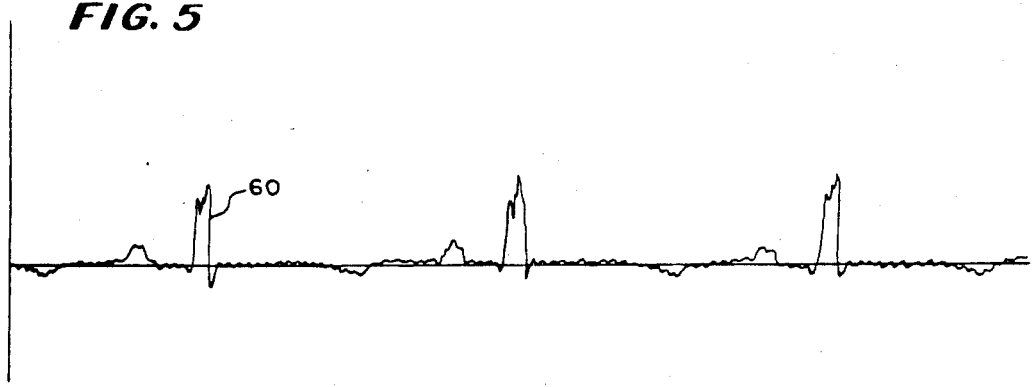
FIG. 5 illustrates an electrocardiogram (EKG) generated by the action of a dog's heart.

Referring to FIG. 1, there is illustrated therein a unipolar pacing lead 8 having a sensor 10 incorporated into a catheter body 12 of the lead 8. The catheter body 12 is of conventional length and size or diameter and is capable of being inserted into an appropriate blood vessel for insertion to a desired position in a heart. A tip electrode 14 is mounted at distal end 15 of the lead 8. Of course, if desired, bipolar pacing electrodes can be provided on or near the distal end of the lead 8.

As is conventional, the pacing tip electrode 14 is connected by a coiled wire conductor 16 (FIG. 2) within the conventional hollow center or lumen 18 (FIG. 2) of the catheter body 12. The coiled wire conductor 16 extends from the distal end 15 to a proximal end 20 (FIG. 1) of the lead 8 where it is connected to pin electrode 22 adapted to be inserted into a conventional pacemaker or, if desired, other electronic circuitry.

The sensor 10 is preferably incorporated directly into the body 12 of the lead 8, which as is conventional, may be made of a medical grade silicon rubber, polyurethane, or the like. Preferably, the sensor 10 is in the form of a piezoelectric bimorph 24 located between an outer wall 25 of the lead 8 and an inner cylindrical surface 27 defining a wall surface 27 of the lumen 18. The bimorph 24 as shown in FIG. 3, has a pair of ceramic sheets 26 and 28 made of suitable piezoelectric materials, such as barium titanate, lead titanate zirconate, lead metaniobate and/or sodium bismuth titanate. As is conventional, the piezoelectric sheets 26 and 28 are separated by a shim 30 of material such as brass. Such a suitable bimorph 24 can be obtained from Piezoelectric Products Inc., or from Vernitron Piezoelectric Division. The bimorph's upper and lower surfaces 32 and 34 are composed of fired on silver or electroless nickel to which a pair of insulated wires 36 and 38 are secured, such as by silver soldering, welding, crimping, or with conductive adhesive. These wires 36 and 38 are incorporated in the body 12 and extend to the proximal end 22, wherein they are similarly connected to a pair of ring or sleeve connectors 40 and 42 (FIG. 1). From there, conventional ring connectors in a socket of a pacer (not shown) which can be of the type disclosed in the Peers-Trevarton U.S. Pat. Nos. 4,458,695 and 4,469,104 the disclosures of which are incorporated herein by reference will connect the sleeves 40 and 42 to appropriate electronic circuitry in the pacer.

The exact placement of the bimorph 24 along the length of the lead 12 is dependent upon what is desired to be monitored. For example, if the sensor 10 is to monitor the activity of the tricuspid valve 50 (FIG. 4) between the right atrium 52 and the right ventricle 54, the bimorph 24 would be placed a distance of approximately 7 to 8 centimeters from the distal end of the lead 8 to be just below the tricuspid valve as shown by sensor 24a in FIG. 4. If, for example, the pressure of blood in the ventricle is to be monitored, the bimorph 24 would be placed closer to the distal end 15, say 1 to 3 centimeters, so that it will be located within the ventricle 54 and just above the apex or bottom of the ventricle 59 as shown by sensor 24b in FIG. 4. Likewise, if the interest was the pressure of blood in the atrium 52, the bimorph 24 could be placed even farther from the distal end, say 9 to 11 centimeters therefrom, so as to be located in the atrium 52.

It is important to note that the bimorph 24 is totally encapsulated within the lead body 12, so that it is isolated from the blood, and yet is still able to sense any pressure changes as a result of the opening and closing of the tricuspid valve 50. This is because the bimorph 24, rather than measuring an accurate absolute pressure, functions somewhat like a microphone, or more like a sonar pickup, to pick up pressure pulses and waves generated by the opening and closing of the tricuspid valve 50, and travelling through the blood, through the encapsulating silicone rubber to the bimorph 24, where it stresses the same and generates an electrical waveform. The encapsulation material is such that pressure pulses or waves can travel therethrough and be transmitted to the bimorph, recoverably stressing the same, to generate electrical waveform signals. Preferably, the wall thickness of the catheter body is less than one millimeter and the thickness of the encapsulation material on the outer facing surface of the bimorph 24 is less than 0.2 millimeter so as to not unduly diminish the pressure pulse or wave to be sensed.

The lead 8 with sensor 10 (bimorph 24) lends itself to telemetering of the waveform for waveform analysis, and to interpretation analysis and utilization of the waveform for determining cardiac parameters, such as cardiac output.

In FIG. 5 is shown a copy of an electrocardiogram (EKG) 60 generated by the action of a dog's heart. The waveform 69 is an electrocardiogram of the electrical activity of the dog's heart occurring during a ventricular contraction.

Figure 6:
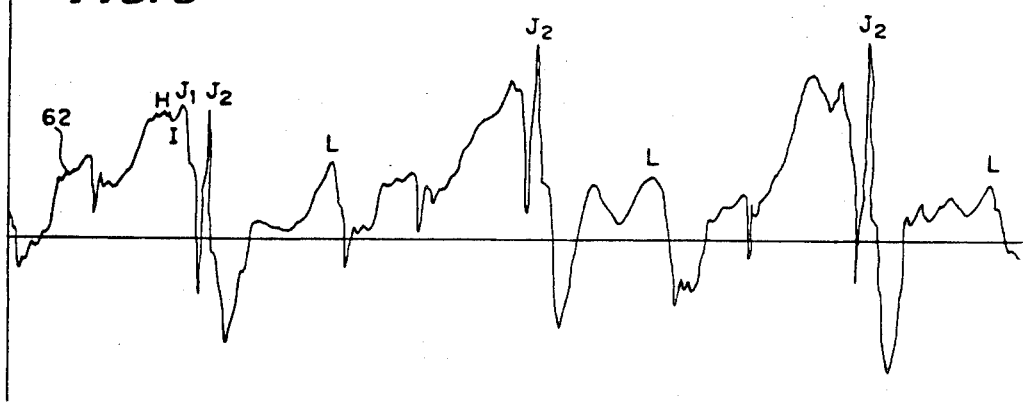
FIG. 6 is a graph of the waveform generated by the sensor in the lead shown in FIG. 1 when the sensor is located just above the apex of the right ventricle, and shows the opening and closing of the semilunar valves in the heart correlated with the EKG activity shown in FIG. 5.

In FIG. 6 is shown, a waveform 62 generated by and recorded from the bimorph 24b located just above the apex of the ventricle 54.

The waveform 62 shows several important heart functions. In this respect, $J_2$ marks the opening of the semilunar valve and L marks the closure of the semilunar valve. Also, the H wave of the vibrocardiogram or waveform 62 occurs simultaneously with the onset of left ventricular isometric contraction.

In animal stuides, such a waveform or vibrocardiogram 62 obtained with a microphone, correlated very well with periods of heart activity measured more accurately with other methods. For example, $H-J_2$ equals the period of isometric contractions; $J_2-L$ equals ejection time; $H-L$ equals systole, $L-H$ equals diastole; and $J_1-J_2$ equals rapid ventricular ejection.

One of the important periods is the ejection time, $J_2-L$ since this period can be used to determine stroke volume which is then used to determine cardiac output so that a doctor can determine the effectiveness of the ventricular, atrial or dual atrial-ventricular pacing in assisting cardiac output.

In this respect, it has been determined that stroke volume times heart rate equals cardiac output. Here, reference is made to the article "Measurement of Stroke Volume by the Videocardiogram" by Agress et al which appeared in the December 1967 issue of Aerospace Magazine. From the studies made by Agress et al, it has been found that:

$$\text{Stroke volume } (SV) = 0.32(J_2 - L) - 19.9$$

Similarly, changes in stroke volume can be defined as follows:

$$\Delta(SV) = 0.30[\Delta(J_2 - L)] + 0.63$$

If desired, the isovolumetric contraction time $(H-J_2)$ can be included in the determination of stroke volume using the videocardiogram although it is not certain that one can obtain a more accurate determination of stroke volume by utilizing $H-J_2$ as well as $J_2-L$ time periods.

Again, stroke volume times heart rate yields cardiac output, a well established indication of heart pumping effectiveness and the pacing of the heart to assist heart pumping.

Figure 7:
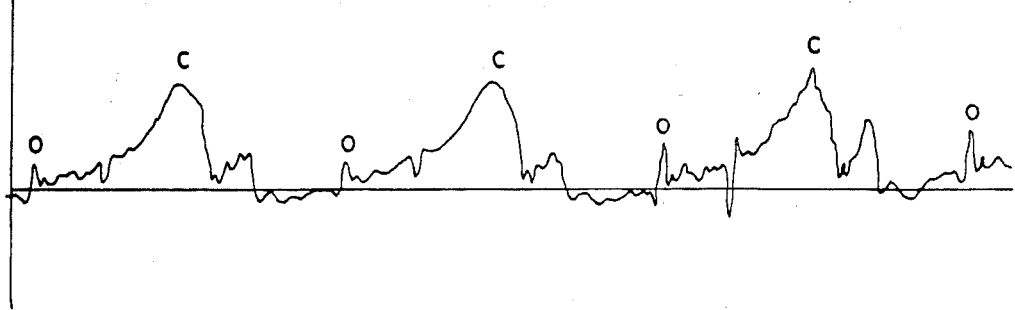
FIG. 7 is a graph similar to the graph of FIG. 5 of the waveform generated by the sensor when it is located just below the tricuspid valve correlated with the EKG activity shown in FIG. 5.

FIG. 7 is a waveform 64 which is generated by sensor 24a located just above the tricuspid valve 50. Although not known with absolute certainty, it is believed that O represents opening of the tricuspid valve and C represents closing of the tricuspid valve.

The sensor 10 of the present invention can be used to measure absolute and/or relative values of the phenomena being sensed, such as valve openings and closings, by viewing the resultant waveforms or traces 62 or 64 obtained with the bimorphs 24b or 24a located at various positions in the heart and such waveforms provide useful and valuable information. The comparison between various generated traces provides a physician with a powerful tool in analyzing any changes in a patient's condition, e.g., change in ejection time. The primary phenomenon measured in a heart is the change in blood pressure in one of the heart chambers as the heart contracts and expands.

Figure 8:
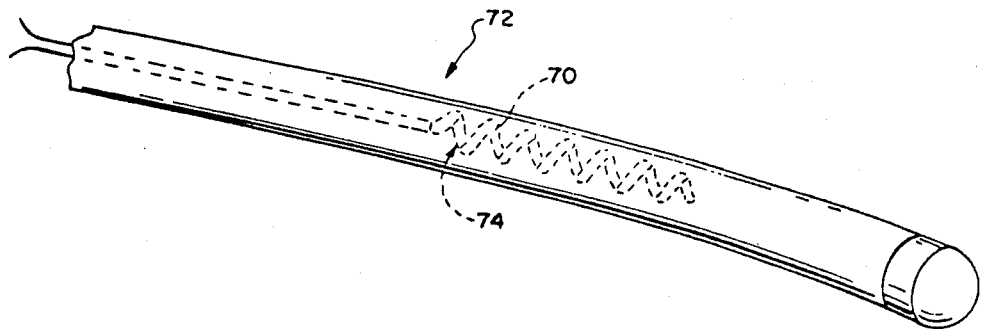
FIG. 8 is a perspective view of a distal end portion of a pacing lead and shows a sensor therein in the form of a thin film polymer piezoelectric strip mounted in a spiral or corkscrew configuration in the pacing lead distal end portion.

Also, the sensor 10 of the present invention can be made in other forms than a piezoelectric bimorph 24. In this respect, the sensor 10 can be realized by a piezoelectric strip 70 constructed of a thin film polymer, e.g. polyvinylidene fluoride ($PVF_2$) and mounted in a pacing lead distal end portion 72 in a spiral or corkscrew configuration 74 as shown in FIG. 8.

Figure 9:
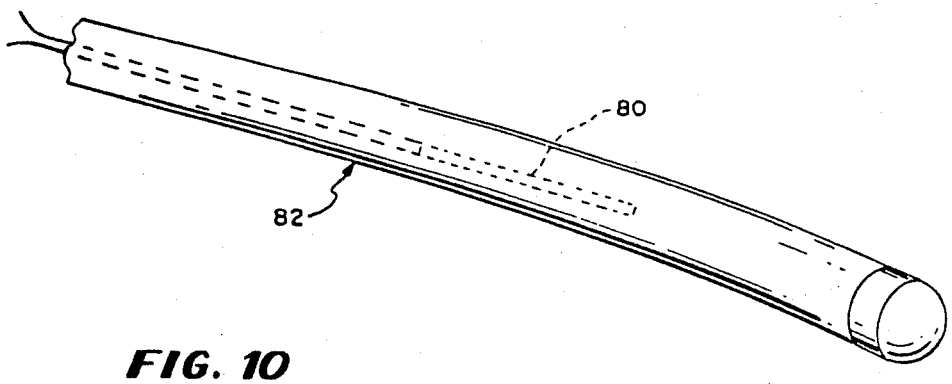
FIG. 9 is a perspective view of a distal end portion of a pacing lead and shows a sensor therein in the form of a thin film polymer piezoelectric elongate strip mounted coaxially of the pacing lead distal end portion.

Alternatively, a straight piezoelectric strip 80 constructed of a thin film polymer, e.g. polyvinylidene fluoride ($PVF_2$) can be used for the sensor 10 and mounted in and coaxially of the elongate axis of a pacing lead distal end portion 82 as shown in FIG. 9.

Of course, the sensor 10 of the present invention can be designed for monitoring other cardiac functions besides changes in blood pressure, such as monitoring atrial or ventricular contractions, opening or closing of other cardiac valves, measuring blood turbulence, or other cardiac activity. Also, the sensor 10 can be incorporated in other than a cardiac lead 8, and could be used to sense phenomena occurring in various parts of the body, such as in the ventricles of the brain or the urinary bladder.

Figure 10:
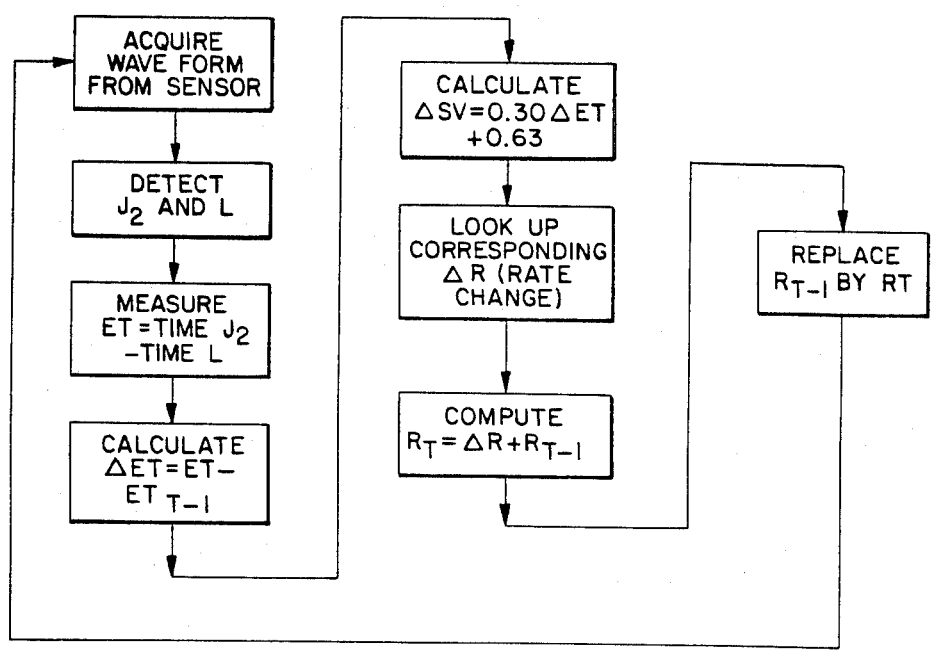
FIG. 10 is a flow chart of the routine or algorithm carried out by the microprocessor in the pacer shown in FIG. 4 for controlling the pacer in response to changes in stroke volume.

Also, it will be understood that the waveforms obtained can be analyzed by a microprocessor in a body implanted pacemaker or a pacer, such as pacer 90 with microprocessor 92 shown in FIG. 4, or in an external signal processing circuit and the openings and closings of particular valves, e.g., semilunar valves or tricuspid valves, in the heart can be determined and this information can be utilized for controlling the pacing pulses, particularly the rate thereof, supplied to the electrode 14 as shown in FIG. 10. A conventional pacing circuit will include the electrode 14 and an indifferent electrode such as the pacer case 93 (FIG. 4) or a ring electrode 94 (FIG. 4) on the lead 81 control circuitry in the pacer 90 including the microprocessor 92 and conventional pulse generating circuitry as disclosed in the Purdy U.S. Pat. No. 3,649,367 (anode pole is at the pulse generator—i.e., at the casing) and the Heilman et al U.S. Pat. No. 4,303,075 (pulse generator and pairs of electrodes), the disclosures of which are incorporated herein by reference.

While one preferred embodiment of a pacing lead 8 with a sensor 10 has been illustrated and described above, it is to be understood that variations and modifications and equivalent structure can be made without departing from the teachings of the present invention. Accordingly, the scope of the invention is only to be limited as necessitated by the accompanying claims.

I claim:

1. An apparatus for sensing pressure changes in a heart chamber to determine opening and closing of a tricuspid valve in a heart, for using those determinations of openings and closings of the tricuspid valve to determine stroke volume and changes in stroke volume, and for controlling pacing of a heart relative to changes in stroke volume, said apparatus comprising: a pacer having therein pulse generating circuitry for generating pacing pulses, control circuitry for controlling the pulse generating circuitry and a socket; a pacing lead having a proximal termination received in said pacer socket, being electrically coupled to said pacer in said socket and having a lead body; a pressure sensor mounted in said lead body; a pacing electrode on said lead body; means for establishing a pacing circuit including said pacing electrode, said pulse generating circuitry and said control circuitry; said control circuitry including circuit means in said pacer coupled to said sensor for sensing changes in pressure in a heart chamber to determine the opening of a tricuspid valve during each heart cycle and the closing of the tricuspid valve during each heart cycle; means for calculating ejection time from the openings and closings of the tricuspid valve; means for calculating the changes in ejection time, $\Delta ET$, from calculations of ejection time; means for calculating changes in stroke volume, $\Delta SV$ from calculations of ejection time; means for determining the required change in heart rate, $\Delta R$, relative to the changes in stroke volume, $\Delta SV$; and means in said control circuitry for adjusting the pacing rate of said pacer relative to the required change in heart rate, $\Delta R$.

2. The apparatus of claim 1 wherein said socket had ring connectors positioned therein; said lead body is flexible and comprises: a generally cylindrical outer wall surface, a lumen within and extending the length of said lead body, a given wall thickness, a proximal end, a proximal end portion, a distal end, and a distal end portion; said pacing electrode includes a tip electrode mounted at said distal end of said lead body for pacing a heart muscle; said lead further includes: a terminal pin extending from said proximal end of said lead body; first and second spaced apart metallic sleeve connectors on said proximal end portion; a pacer wire conductor within said lumen of said lead body and having a distal end connected to said tip electrode and a proximal end adapted to be connected to said pacer through said terminal pin; said sensor comprises a piezoelectric pressure sensing means mounted in said lead body distal end portion adjacent to said outer wall surface and at a pre-determined distance behind said tip electrode for generating, from inside the heart, a wave-form of heart activity in response to changes in right ventricular blood pressure, said waveform showing openings and closings of the tricuspid valve in the right ventricle of a heart when said lead body distal end portion is received in the right ventricle of a heart; said lead also has: first and second wire conductors in said lead body, each wire conductor having a distal end connected to said piezoelectric pressure sensor means and a proximal end connected to said first or second sleeve connector and said sleeve connectors being electrically isolated from each other and electrically isolated from said terminal pin; and said sleeve connectors received in said socket in said pacer make contact with said ring connectors positioned in said socket.

3. An apparaus for sensing pressure changes in a heart chamber to determine opening and closing of a tricuspid valve in a heart, for using those determinations of openings and closings of the tricuspid valve to determine stroke volume and changes in stroke volume, and for controlling pacing of a heart relative to changes in stroke volume, said apparatus comprising: a pacer having therein pulse generating circuitry for generating pacing pulses, control circuitry for controlling the pulse generating circuitry therein and a socket, a pacing lead having a proximal termination received in said pacer socket, being electrically coupled to said pacer in said socket and having a lead body; a pressure sensor mounted in the lead body; a pacing electrode on said lead body; means for establishing a pacing circuit including said pacing electrode, said pulse generating circuitry and said control circuitry; said control circuitry including circuit means in said pacer coupled to said sensor for sensing changes in pressure in a heart chamber to determine the opening of the tricuspid valve during each heart cycle and the closing of the tricuspid valve during each heart cycle; means for calculating ejection time from the openings and closing of the tricuspid valve; means for calculating the changes in ejection time, $\Delta ET$, from determinations of ejection time; means for calculating changes in stroke volume, $\Delta SV$ from calculations of ejection time, from the formula:

$$\Delta SV = 0.30(\Delta ET) + 0.63;$$

means for determining the required changes in heart rate, $\Delta R$, relative to the change in stroke volume, $\Delta SV$; and means in said control circuitry for adjusting the pacing rate of the pacer relative to the required change in heart rate, $\Delta R$.

* * * * *